US00PP23326P3

(12) United States Plant Patent
Bell

(10) Patent No.: US PP23,326 P3
(45) Date of Patent: Jan. 15, 2013

(54) BLUEBERRY PLANT NAMED 'RIDLEY 1104'

(50) Latin Name: ***Vaccinium* hybrid**
Varietal Denomination: Ridley 1104

(75) Inventor: Ridley Bell, Lindendale (AU)

(73) Assignee: Mountain Blue Orchards Pty Ltd., New South Wales (AU)

( * ) Notice: Subject to any disclaimer, the term of this patent is extended or adjusted under 35 U.S.C. 154(b) by 65 days.

(21) Appl. No.: 12/930,908

(22) Filed: Jan. 18, 2011

(65) Prior Publication Data

US 2011/0185460 P1 Jul. 28, 2011

Related U.S. Application Data

(60) Provisional application No. 61/336,458, filed on Jan. 22, 2010.

(51) Int. Cl.
*A01H 5/00* (2006.01)

(52) U.S. Cl. ..... Plt./157

(58) Field of Classification Search ..... Plt./157
See application file for complete search history.

(56) References Cited

U.S. PATENT DOCUMENTS

| | | | |
|---|---|---|---|
| PP10,675 | P | 11/1998 | Lyrene |
| PP20,642 | P2 | 1/2010 | Wright |
| PP20,695 | P2 | 2/2010 | Wright |
| PP22,757 | P3 | 5/2012 | Wright |

*Primary Examiner* — June Hwu

(74) *Attorney, Agent, or Firm* — Davis Wright Tremaine LLP; Dale C. Hunt; Wenhua Yu

(57) ABSTRACT

A new and distinct cultivar of *Vaccinium* hybrid plant named 'RIDLEY 1104', characterized by its combination of spreading plant shape and strong plant growth vigor, evergreen foliage with broad leaves, early to medium timing of flowering and fruiting, medium to large fruit size, firm fruit suited to handling, attractive dark blue fruit color, medium to high berry sweetness and small picking scar.

2 Drawing Sheets

Latin name of genus and species of plant claimed: *Vaccinium* hybrid.

Variety denomination: 'Ridley 1104'.

BACKGROUND OF THE INVENTION

The present invention relates to a new and distinct perennial variety of *Vaccinium* hybrid (Southern Highbush Blueberry), which has been given the variety denomination of 'Ridley 1104'. Its market class is that of a fruiting plant. 'Ridley 1104' is intended for use as fresh fruit for shipping, customer pick and processing markets and as a home garden plant.

The new *Vaccinium* hybrid cultivar is a selection resulting from seedlings produced in a controlled breeding programme of *Vaccinium* at Lindendale, NSW, Australia in 2003 from the controlled pollination of seed parent 'C97-390' (U.S. Plant Pat. No. 20,642) and pollen parent 'C97-41' (U.S. Plant Pat. No. 22,757). The new cultivar was selected as a single plant within a population of plants resulting from this controlled pollination of *Vaccinium* hybrids in 2005 in a commercial field plantation environment at Lindendale, New South Wales, Australia. Selection criteria was a combination of strong plant growth vigor, low chilling requirement, early to medium season of flowering and fruiting, firm fruit suited to handling, sweet berries and small picking scar. The selection was subsequently evaluated for a number of years at the commercial farms at Lindendale, New South Wales, Australia.

Asexual reproduction of the new cultivar by cutting propagation since 2005 at Lindendale, New South Wales, Australia and has demonstrated that the new cultivar reproduces true to type with all of the characteristics, as herein described, firmly fixed and retained through successive generations of such asexual propagation.

The new variety can be compared to the seed parent 'C97-390' (U.S. Plant Pat. No. 20,642). In Lindendale, New South Wales, Australia the time of both flowering and fruit ripening of 'Ridley 1104' is classified as 'early to medium' whereas the time of flowering and fruit ripening of 'C97-390' is classified as 'very early to early'. The berry diameter of 'Ridley 1104' is 'medium to large' whereas the berry diameter of 'C97-390' is 'medium'. The new variety can also be compared to the pollen parent 'C97-41' (U.S. Plant Pat. No. 22,757). In Lindendale, New South Wales, Australia the time of flowering of 'Ridley 1104' is classified as 'early to medium' whereas the time of flowering of 'C97-41' is classified as 'early'. The berry diameter of 'Ridley 1104' is 'medium to large' whereas the berry diameter of 'C97-41' is 'medium'.

The new variety has been primarily compared to the variety 'C99-42' (U.S. Plant Pat. No. 20,695). In Lindendale, New South Wales, Australia the time of beginning of flowering of 'Ridley 1104' is classified as 'early to medium' whereas the time of beginning of flowering of time of 'C99-42' is classified as 'very early to early'. The time of fruit ripening of 'Ridley 1104' is classified as 'early to medium' whereas the time of fruit ripening of 'C99-42' is classified as 'early'. The leaf length of 'Ridley 1104' is 'medium to long' whereas the leaf length of 'C99-42' is 'medium'. The leaf width of 'Ridley 1104' is 'broad' whereas the leaf width of 'C99-42' is 'narrow to medium'. The berry diameter of 'Ridley 1104' is 'medium to large' (mean 16.2 mm) whereas the berry diameter of 'C99-42' is 'medium' (mean 15.5 mm). The berry sweetness of 'Ridley 1104' is 'medium to high' whereas 'C99-42' is 'low to medium'. This combination of vegetative and fruiting attributes results in 'Ridley 1104' being a desirable variety for very early to medium season commercial production. See Table 1 for comparisons.

'Ridley 1104' can be compared to the variety 'Star' (U.S. Plant Pat. No. 10,675). The plant growth vigour of 'Ridley 1104' is 'strong' whereas the plant growth vigour of 'Star' is 'medium'. The plant growth habit of 'Ridley 1104' is spreading whereas the plant growth habit of 'Star' is upright. The leaf length of 'Ridley 1104' is medium to long whereas the leaf length of 'Star' is medium. The leaf width of 'Ridley 1104' is broad whereas the leaf length of 'Star' is narrow. The berry diameter of 'Ridley 1104' is medium to large (mean 16.2 mm) whereas the berry diameter of 'Star' is large (mean 18.1 mm). The average berry weight of 'Ridley 1104' is 1.9 g whereas the average berry weight of 'Star' is 2.3 g. The berry calyx basin diameter of 'Ridley 1104' is small to medium (mean 5.5 mm) whereas the berry calyx basin diameter of 'Star' is large to very large (mean 8.8 mm). The berry calyx basin depth of 'Ridley 1104' is deep whereas the berry calyx basin depth of 'Star' is shallow. The berry sweetness of 'Ridley 1104' is 'medium to high' whereas 'Star' is 'low to medium'.

SUMMARY OF THE INVENTION

The following characteristics of the new cultivar have been repeatedly observed and can be used to distinguish 'RIDLEY 1104' as a new and distinct cultivar of *Vaccinium* hybrid plant:

1. Spreading plant growth habit
2. early to medium timing of beginning of flowering
3. early to medium timing of fruit ripening
4. Strong plant growth vigour
5. Dark blue berry color
6. Berry firmness is firm
7. Picking scar is dry
8. Leaf width is broad
9. Berry size is medium to large
10. Berry sweetness is medium to high

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'RIDLEY 1104'.

DETAILED BOTANICAL DESCRIPTION

Figure 1:
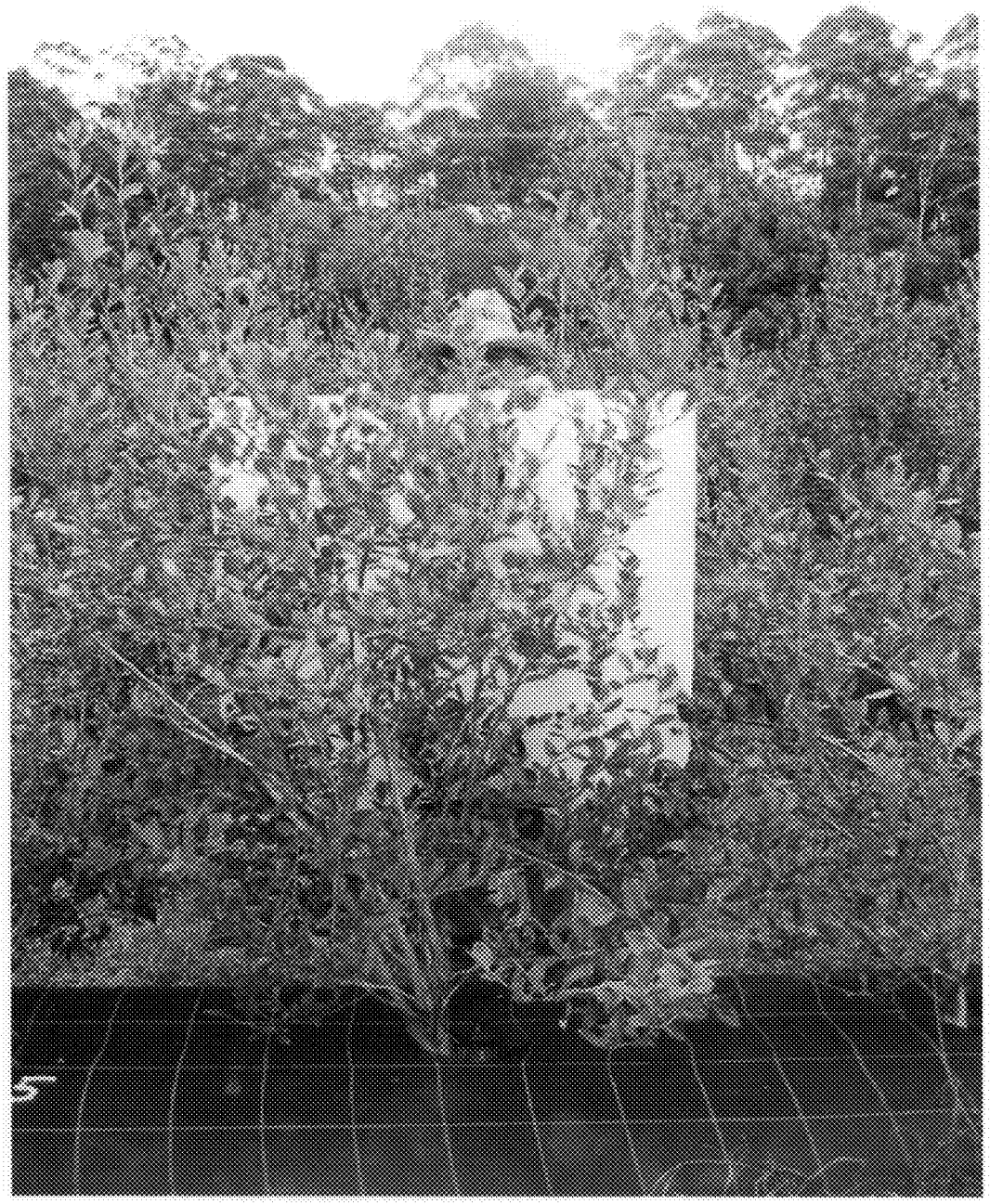
FIG. 1 illustrates a 'RIDLEY 1104' bush in a commercial field planting.
Figure 2:
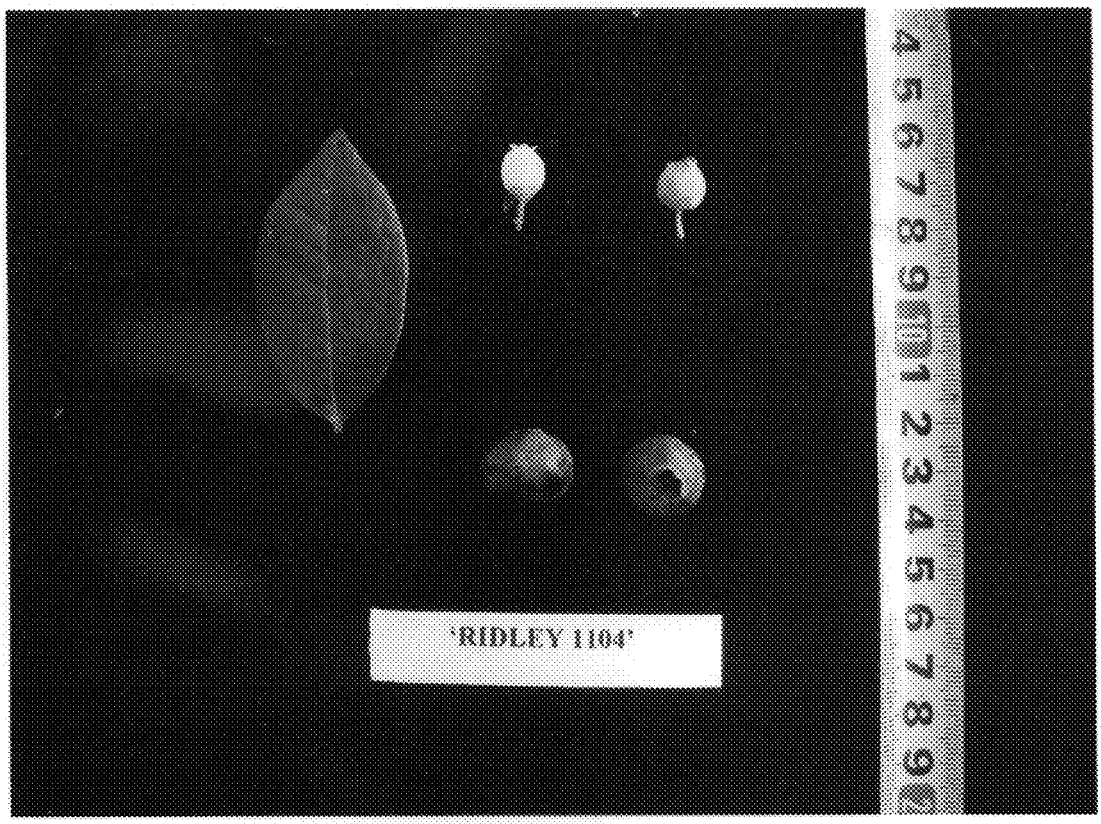
FIG. 2 illustrates a 'RIDLEY 1104' leaf, berry and flower shape and dimensions.

The following is a detailed botanical description of a new and distinct variety of an *Vaccinium* hybrid ornamental plant known as 'RIDLEY 1104'. Plant observations were made on plants grown in Lindendale, New South Wales, Australia. Unless indicated otherwise, the descriptions disclosed herein are based upon observations made in August 2009 of mature 'RIDLEY 1104' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'RIDLEY 1104' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Vaccinium* hybrid cultivar RIDLEY 1104.

Parentage:

*Parents*.—Seed parent 'C97-390' (U.S. Plant Pat. No. 20,642); pollen parent 'C97-41' (U.S. Plant Pat. No. 22,757).

Plant:

*Growth habit*.—Spreading.
*Growth vigor*.—Is strong.
*Plant height*.—Is approximately 1.9 m.
*Plant width*.—Is approximately 1.5 m.
*Flower bud density*.—Is medium.
*Twigginess*.—Is low.
*Time of beginning of flowering*.—Is early to medium (begins early May; peaks late July) when grown as an evergreen in Australia.
*Time of fruit ripening*.—Is early to medium (begins mid June; peaks late September) when grown as an evergreen in Australia.

Stem:

*Suckering tendency*.—Plants typically have 5-7 major canes per plant from a base 25 cm in diameter on 5 year old plants.
*Canes*.—Semi-erect with moderate branching; color greyed orange 198C; 2 year old cane diameter 12 mm, colored greyed orange 177B, some flaking of bark, current season wood diameter 3-4 mm, colored yellow green 144C.
*Internode length on strong, new shoots*.—15-20 mm.
*Fruiting wood*.—Numerous twigs to 10 cm in length.
*Surface texture of new wood*.—Smooth.

Fully developed leaf:

*Length*.—Medium to long 60-70 mm.
*Width*.—Broad approximately 40 mm.
*Shape*.—Elliptic.
*Color of upper surface*.—Yellow green 137A.
*Color of lower surface*.—Yellow green 148C.
*Intensity of color*.—Medium.
*Margin*.—Entire.
*Undulation of margin*.—Weak.
*Pubescence of upper side*.—Absent.
*Pubescence of lower side*.—Absent.
*Cross sectional profile*.—Flat.
*Longitudinal profile*.—Straight.
*Attitude*.—Broad acute to horizontal.
*Shape of apex*.—Is acuminate.
*Shape of base*.—Is obtuse.

Inflorescence:

*Length of peduncle*.—To 12 mm.
*Length of pedicel*.—Long 4-6 mm.
*Number of flowers per cluster*.—Median 7.
*Flower cluster density*.—Is medium.
*Diameter*.—20-30 mm.
*Length*.—30-50 mm.
*Color of peduncle*.—146C.

*Texture of peduncle*.—Is smooth.
*Color of pedicel*.—146C.
*Texture of pedicel*.—Is smooth.

Flowers:
*Length of bud*.—Medium (to 12 mm), bud shape tubular, oblong with acute apex.
*Bud color*.—Green 138A (calyx) with white 155D corolla.
*Length of corolla tube*.—Medium to long (to 15 mm).
*Width of corolla tube*.—Medium to broad (to 11 mm).
*Corolla aperture diameter*.—3-4 mm.
*Color of corolla*.—White 155D.
*Anthocyanin coloration of corolla*.—Absent.
*Corolla ridges*.—Present.
*Protusion of stigma*.—Absent.
*Fragrance*.—Weak.
*Shape*.—Urceolate.
*Abundance of pollen*.—High.
*Calyx (with sepals) diameter*.—5-6 mm.
*Calyx color*.—Green 138A.

Productivity: 3 to 4 kg per season from 3-4 year old plants planted at 3.0 m×0.9 m density.

Cold hardiness: RIDLEY 1104 has not been grown in all environments including harsh winter environments. Cold tolerance is expected to be low.

Chilling requirement: RIDLEY 1104 has not been grown in all environments and is typically grown as an evergreen crop where chilling hours are not important. RIDLEY 1104 is classed as 'low chill', typical of Southern Highbush Blueberry varieties with an estimated chilling requirement of 250 hours (not tested).

Leafing: Plants retain leaves year round (at Lindendale, NSW Australia) and RIDLEY 1104 is grown commercially as an evergreen crop. New leafing occurs in mid to late August at Lindendale, NSW Australia.

Fruit:
*Unripe fruit color intensity*.—Light.
*Unripe fruit color*.—144A.
*Cluster density*.—Is medium.
*Diameter*.—Is medium to large (mean 16.2 mm).
*Weight*.—Medium (approximately 1.9 g).
*Shape*.—Round.
*Attitude of calyx*.—Erect.
*Diameter of calyx basin*.—Medium (mean 5.5 mm).
*Depth of calyx basin*.—Is deep (to 2.2 mm).
*Intensity of bloom*.—Strong.
*Intensity of blue color of skin with bloom removed*.—Is very dark.
*Color of skin*.—202A.
*Sweetness when ripe*.—Medium to high.
*Color of flesh when ripe*.—Yellow green 145D to yellow green 150D.
*Firmness when ripe*.—Firm.
*Acidity when ripe*.—Medium.
*Size of scar*.—Is small (1.0-1.5 mm).
*Storage quality*.—Good.

Date of 50% maturity: Approximately 25$^{th}$ August at Lindendale, NSW Australia.

Fruit development period: Approximately 55 days in protected cultivation at Lindendale, NSW Australia.

Seed:
*Seed color*.—Greyed orange 165B.
*Seed abundance in fruit*.—Medium.
*Seed size*.—1.6-1.8 mm long for fully developed seeds.

TABLE 1

Comparison with other varieties (extract from Australian PBR data)

| Organ/Plant Part: Context | Ridley 1104 | C99-42 | Star |
|---|---|---|---|
| Plant: vigour | strong | medium | medium |
| Plant: growth habit | spreading | semi upright | upright |
| Leaf: length | medium to long | medium | medium |
| Leaf: width | broad | narrow to medium | narrow |
| Leaf: shape | elliptic | elliptic | elliptic |
| Leaf: colour of upper side | green | green | green |
| Leaf: intensity of green colour on upper side (varieties with green leaf colour only) | medium | medium | medium |
| Leaf: margin | entire | entire | entire |
| Flower: size of corolla tube | medium to large | medium | medium |
| Flower: anthocyanin colouration of corolla tube | absent or very weak | absent or very weak | absent or very weak |
| Flower: ridges on corolla tube | present | present | present |
| Fruit cluster: density | medium | dense | medium |
| Flower: protusion of stigma | absent | absent | present |
| Unripe fruit: intensity of green colour | light | light | light |
| Fruit: size | medium to large | medium to large | large |
| Fruit: shape in longitudinal section | round | round | round |
| Fruit: attitude of sepals | erect | erect | erect |
| Fruit: diameter of calyx basin | small to medium | medium | large to very large |
| Fruit: depth of calyx basin | deep | medium | shallow |
| Fruit: intensity of bloom | strong | strong | strong |
| Fruit: colour of skin | dark blue | dark blue | dark blue |
| Fruit: firmness | firm | firm | firm |
| Fruit: sweetness | medium to high | low to medium | low to medium |
| Fruit: acidity | medium | medium | medium |
| Fruit: size of scar | small | small | small |
| Fruit: average weight of ripe berry (g) | 1.9 | 1.6 | 2.3 |
| Time of: beginning of flowering on current year's shoot (varieties which fruit on one-year-old and current season's shoots only) | early to medium | very early to early | early to medium |
| Time of: beginning of fruit ripening on current year's shoot (varieties which fruit on one-year-old and current season's shoots) | early to medium | early | early to medium |

What is claimed is:

1. A new and distinct cultivar of *Vaccinium* hybrid plant named 'RIDLEY 1104', substantially as herein shown and described.

* * * * *